United States Patent [19]

Takeda et al.

[11] 4,404,214
[45] Sep. 13, 1983

[54] 2-PYRIDINECARBOXAMIDE DERIVATIVES COMPOSITIONS CONTAINING SAME AND METHOD OF USING SAME

[75] Inventors: Mikio Takeda, Urawa; Yasushi Honma, Ageo; Kei Tsuzurahara, Omiya, all of Japan

[73] Assignee: Tanabe Seiyaku Co., Ltd., Osaka, Japan

[21] Appl. No.: 323,289

[22] Filed: Nov. 20, 1981

[30] Foreign Application Priority Data

Dec. 5, 1980 [JP] Japan ................... 55-172246

[51] Int. Cl.³ .................. C07D 401/12; A61K 31/455
[52] U.S. Cl. .................... 424/266; 546/276; 542/458
[58] Field of Search ............. 542/458; 546/276; 424/266

[56] References Cited

U.S. PATENT DOCUMENTS 4,129,735 12/1978 Sellstedt et al. ............. 546/276
4,332,809 6/1982 Honma et al. ............. 424/266

OTHER PUBLICATIONS

Braude et al., Chem. Abstracts, vol. 49, No. 19,13,149a–13,151-g, Oct. 10, 1955.

Rinderknecht, Helvetica Chimica Acta, vol. 42, pp.-1324-1327 (1959) in German.
Rindernecht, Chem. Abstracts, vol. 54, No. 1, pp.-526h–527-e Jan. 10, 1960.
Klingsberg, Pyridine and its Derivatives, Part 3, Interscience Publishers, pp. 218–219, (1962).

Primary Examiner—Alan L. Rotman
Attorney, Agent, or Firm—Jordan B. Bierman; Linda Bierman

[57] ABSTRACT

A 2-pyridinecarboxamide derivative of the formula:

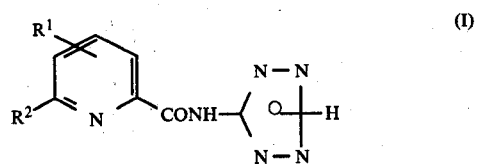

wherein $R^1$ is hydrogen, lower alkyl, lower alkoxy, halogen, lower alkyl-thio or nitro and is in the 3rd-, 4th- or 5th-position of the pyridyl group, and $R^2$ is hydrogen, lower alkyl, lower alkoxy, phenoxy, phenyl-lower alkyl, phenyl-lower alkenyl, or halogen. Said 2-pyridinecarboxamide derivative (I) or a pharmaceutically acceptable salt thereof is useful as an anti-allergic agent.

24 Claims, No Drawings

2-PYRIDINECARBOXAMIDE DERIVATIVES COMPOSITIONS CONTAINING SAME AND METHOD OF USING SAME

This invention relates to a novel 2-pyridinecarboxamide derivative and a process for preparing same. More particularly, it relates to a compound of the general formula:

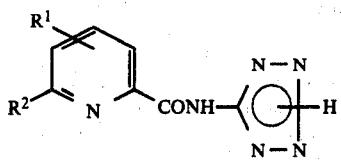

wherein $R^1$ is hydrogen, lower alkyl, lower alkoxy, halogen, lower alkyl-thio or nitro and is in the 3rd-, 4th- or 5th-position of the pyridyl group, and $R^2$ is hydrogen, lower alkyl, lower alkoxy, phenoxy, phenyl-lower alkyl, phenyl-lower alkenyl or halogen, or a pharmaceutically acceptable salt thereof.

The 2-pyridinecarboxamide derivative (I) of the present invention has two isomeric structures: 1H-isomer and 2H-isomer in the tetrazole ring as shown in the following formulae, which are mutually converted from one to another. These isomers are both included within the scope of the present invention.

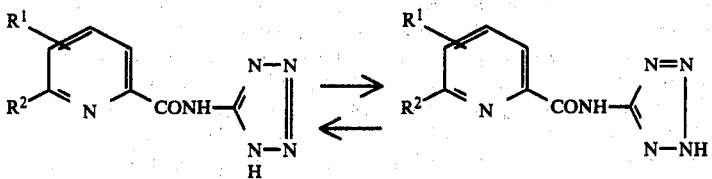

wherein $R^1$ and $R^2$ are the same as defined above.

Helv. Chim. Acta., Vol. 42, pp. 1324-1327 (1959) discloses that nicotinoylaminotetrazole (i.e., N-(5-tetrazolyl)-3-pyridinecarboxamide) is prepared by condensing nicotinic acid with 5-aminotetrazole. However, the above-mentioned literature teaches nothing but the synthesis of nicotinoylaminotetrazole and makes no mention of an anti-allergic activity of said compound.

As a result of various investigations, we have now found that the novel 2-pyridinecarboxamide derivative (I) of the present invention shows potent anti-allergic activity and is useful as an anti-allergic agent.

Representative examples of the 2-pyridinecarboxamide derivative of the invention include those of the formula (I) in which $R^1$ is hydrogen; lower alkyl such as methyl, ethyl, n-propyl, isopropyl or n-butyl; lower alkoxy such as methoxy, ethoxy, n-propoxy or n-butoxy; halogen such as chlorine or bromine; lower alkyl-thio such as methylthio, ethylthio, n-propylthio or n-butylthio; or nitro, and $R^2$ is hydrogen; lower alkyl such as methyl, ethyl, n-propyl or n-butyl; lower alkoxy such as methoxy, ethoxy, n-propoxy or n-butoxy; phenoxy; phenyl-lower alkyl such as benzyl or phenethyl; phenyl-lower alkenyl such as styryl; or halogen such as chlorine or bromine. Among them, a preferred subgenus includes the compound of the formula (I) in which $R^1$ is hydrogen, lower alkyl, lower alkoxy or halogen, and $R^2$ is hydrogen, lower alkyl, lower alkoxy or phenyl-lower alkenyl. Another preferred subgenus includes the compound of the formula (I) in which $R^1$ is hydrogen, lower alkyl or halogen and is in the 3rd- or 4th-position of the pyridyl group, and $R^2$ is hydrogen, lower alkyl or phenyl-lower alkenyl. Another preferred subgenus includes the compound of the formula (I) in which $R^1$ is hydrogen, methyl, ethyl, n-butyl, methoxy, chloro or bromo and is in the 3rd- or 4th-position of the pyridyl group, and $R^2$ is hydrogen, methyl, methoxy or styryl. A further preferred subgenus includes the compound of the formula (I) in which $R^1$ is hydrogen, methyl, ethyl, chloro or bromo and is in the 3rd- or 4th-position of the pyridyl group, and $R^2$ is hydrogen, methyl or styryl. A still further preferred subgenus includes the compound of the formula (I) in which $R^1$ is hydrogen, methyl or chloro and is in the 3rd- or 4th-position of the pyridyl group, and $R^2$ is methyl.

According to the present invention, the 2-pyridinecarboxamide derivative (I) can be prepared by condensing a 2-pyridinecarboxylic acid of the formula:

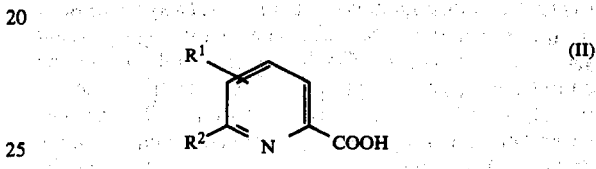

wherein $R^1$ and $R^2$ are the same as defined above, or a reactive derivative thereof with 5-aminotetrazole. Alternatively, the compound (I) in which $R^1$ is hydrogen and $R^2$ is phenethyl can be prepared by condensing a 2-pyridinecarboxylic acid of the formula:

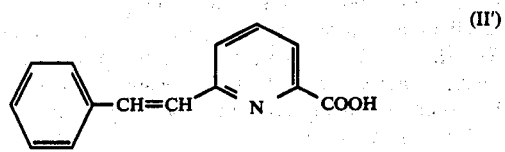

or a reactive derivative thereof with 5-aminotetrazole to give a 2-pyridinecarboxamide derivative of the formula:

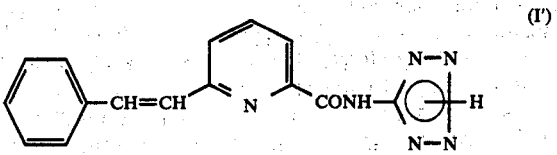

and then subjecting the compound (I') to catalytic hydrogenation.

The condensation reaction of the 2-pyridinecarboxylic acid (II) or (II') with 5-aminotetrazole can be readily accomplished. For example, said condensation reaction is preferably carried out in the presence of a dehydrating agent in a solvent. Suitable examples of the dehydrating agent include N,N'-dicyclohexylcarbodiimide, N,N'-carbonyldiimidazole, or the like. Tetrahydrofuran, dioxane, dimethylformamide and a mixture thereof are suitable as the solvent. It is preferred to carry out the reaction at a temperature between −10° C. and 100° C.

Alternatively, the 2-pyridinecarboxylic acid (II) or (II') may be converted to the reactive derivative thereof prior to the condensation reaction mentioned above. Suitable examples of the reactive derivative of the 2-pyridinecarboxylic acid (II) or (II') include the corresponding halide and mixed anhydride. The halide of the 2-pyridinecarboxylic acid (II) or (II') may be prepared in conventional manners, for example, by reacting said acid with a halogenating agent such as thionyl chloride, phosphorus oxychloride or phosphorus pentachloride. The reaction may be preferably carried out at a temperature between 0° C. and the reflux temperature of the halogenating agent in a solvent. Benzene, toluene or pyridine are suitable as the solvent. When an excess of the halogenating agent is used, it is not always necessary to use the solvent because said halogenating agent serves as the solvent. On the other hand, the mixed anhydride may be prepared by reacting the 2-pyridinecarboxylic acid (II) or (II') with alkyl chlorocarbonate (e.g., ethyl chlorocarbonate, isobutyl chlorocarbonate) at a temperature of −30° to 20° C. in the presence of an acid acceptor (e.g., triethylamine, N-methylmorpholine) in a solvent (e.g., tetrahydrofuran, dioxane, methylene chloride). The condensation reaction of the halide of the 2-pyridinecarboxylic acid (II) or (II') with 5-aminotetrazole is carried out in the presence of an acid acceptor in a solvent. Suitable examples of the acid acceptor include an organic base such as triethylamine or pyridine, and an alkali metal carbonate such as sodium bicarbonate or sodium carbonate. Dimethylformamide, methylene chloride, dioxane and the like are suitable as the solvent. When an excess of the organic base is employed as the acid acceptor, it is not always necessary to use the solvent because said organic base serves as the solvent. It is preferable to carry out the reaction at a temperature between 0° C. and 120° C. On the other hand, the condensation reaction of the mixed anhydride of the 2-pyridinecarboxylic acid (II) or (II') with 5-aminotetrazole is carried out in a solvent. Tetrahydrofuran, dioxane, dimethylformamide or a mixture thereof are suitable as the solvent. It is preferable to carry out the reaction at a temperature between −30° C. and 20° C.

The catalytic hydrogenation of the compound (I') can be readily accomplished. For example, said catalytic hydrogenation is preferably carried out in the presence of a catalyst in a hydrogen atmosphere. Suitable examples of the catalyst include palladium-carbon, palladium-black and so forth. A mixture of water and alkanol (e.g., methanol, ethanol) is suitable as the solvent. It is also preferable to carry out the reaction under a pressure of 1-10 atmospheres.

As described hereinbefore, the 2-pyridinecarboxamide derivative (I) of the present invention shows anti-allergic activity. Especially, said derivative (I) shows a potent inhibiting activity against immediate-type allergic response. For example, the 2-pyridinecarboxamide derivative (I) inhibits passive cutaneous anaphylaxis, systemic anaphylaxis, anaphylactic (or antigen-induced) broncho-constriction, allergic skin hypersensitivity and anaphylactic histamine release. When the anti-allergic activity is estimated by passive cutaneous anaphylaxis (PCA) reaction in rats using anti-Ascaris suum antiserum, the 2-pyridinecarboxamide derivative (I) shows the PCA inhibition more than 10 times stronger than that of N-(5-tetrazolyl)-3-pyridinecarboxamide disclosed in Helv. Chim. Acta, 42, 1324–1327 (1959). Moreover, the 2-pyridinecarboxamide derivative (I) is low in toxicity and has a great margin of safety for use as an anti-allergic agent. For example, the 50% lethal dose ($LD_{50}$) of N-(5-tetrazolyl)-6-methyl-2-pyridinecarboxamide sodium salt which is estimated by oral administration thereof to mice is about 800 mg/kg. Further, the 2-pyridinecarboxamide derivative (I) shows no substantial decrease in its anti-allergic activity (i.e., no substantial tolerance) even after repeated use thereof and can be used without undesirable side effects. Therefore, the 2-pyridinecarboxamide derivative (I) is useful for the treatment and/or prophylaxis of various allergic symptoms such as allergic bronchial asthma, urticaria, allergic eczema, hay fever, allergic rhinitis and the like.

The 2-pyridinecarboxamide derivative (I) can be used for pharmaceutical use as the free form or a salt thereof. Pharmaceutically acceptable salts of the 2-pyridinecarboxamide (I) include, for example, alkali metal salts such as sodium, potassium and lithium salts, organic amine salts such as triethanolamine and tris(hydroxymethyl)aminomethane salts, and basic amino acid salts such as lysine salt. These salts can be readily prepared by treating the 2-pyridinecarboxamide (I) with an alkali metal hydroxide (e.g., sodium hydroxide, potassium hydroxide, lithium hydroxide), an alkali metal carbonate (e.g., sodium carbonate, potassium carbonate, sodium bicarbonate), an organic amine (e.g., triethanolamine, tris(hydroxymethyl)aminomethane) or a basic amino acid (e.g., lysine). The 2-pyridinecarboxamide derivative (I) or a salt thereof can be administered either orally or parenterally. A daily dose of the 2-pyridinecarboxamide derivative (I) or a salt thereof may be about 0.1 mg to about 300 mg, especially about 0.3 mg to about 30 mg, per kilogram of body weight. Further, the 2-pyridinecarboxamide derivative (I) or its salt may be used in the form of a pharmaceutical preparation containing the same derivative in conjunction or admixture with a pharmaceutical excipient suitable for oral or parenteral administration. Suitable excipients include, for example, arabic gum, gelatine, sorbitol, tragacanth gum, polyvinylpyrrolidone, lactose, sucrose, potassium phosphate, magnesium stearate, talc, potato starch and other known medicinal excipients. The pharmaceutical preparation may be in solid form such as tablets, powder, capsules or granules; or in liquid form such as solutions or suspensions. Further, when administered parenterally, the pharmaceutical preparation may be employed in the form of injections.

Practical and presently preferred embodiments of the present invention are illustratively shown in the following Examples. Throughout the specification and claims, the terms "lower alkyl," "lower alkoxy" and "lower alkenyl" should be interpreted as referring to alkyl of one to four carbon atoms, alkoxy of one to four carbon atoms and alkenyl of two to four carbon atoms, respectively.

EXAMPLE 1

5 g of α-picolinic acid are dissolved in 40 ml of thionyl chloride, and the solution is refluxed for 2 hours. After the reaction, the solution is concentrated under reduced pressure to remove excess thionyl chloride. The residue is dissolved in 30 ml of dimethylformamide, and a solution of 4.07 g of 5-aminotetrazole and 8.14 g of triethylamine in 10 ml of dimethylformamide is added thereto under cooling. The mixture is stirred at 70° C. for one hour. Then, the reaction mixture is concentrated under reduced pressure to remove dimethylformamide. Water is added to the residue, and the aqueous mixture is adjusted to pH 2–3 with 10% hydrochloric acid. The crystalline precipitates are collected by filtration, and then recrystallized from a mixture of dimethylformamide and ethyl acetate. 4.22 g of N-(5-tetrazolyl)-2-pyridinecarboxamide are thereby obtained.

M.p. 268.5°–269° C. (decomp.)

2.11 g of N-(5-tetrazolyl)-2-pyridinecarboxamide are dissolved in 11 ml of an aqueous 1 N sodium hydroxide solution, and the aqueous mixture is filtered through activated charcoal. The filtrate is concentrated under reduced pressure to remove solvent. Ethanol is added to the residue, and the crystalline precipitates are collected by filtration. 2.26 g of N-(5-tetrazolyl)-2-pyridinecarboxamide sodium salt are thereby obtained.

M.p. 278°–280° C. (decomp.)

EXAMPLE 2

A mixture of 1.06 g of 4-methyl-2-pyridinecarboxylic acid, 1.28 g of N,N'-carbonyldiimidazole, 25 ml of dimethylformamide and 12 ml of tetrahydrofuran is stirred at room temperature for 3 hours. 0.72 g of 5-aminotetrazole is added to the mixture and said mixture is stirred at 80° C. for 3 hours. Then, the reaction mixture is concentrated under reduced pressure to remove solvent. Water is added to the residue, and the aqueous mixture is adjusted to pH 2 with 10% hydrochloric acid. The crystalline precipitates are collected by filtration, washed with water and then recrystallized from a mixture of dimethylformamide and water. 0.52 g of N-(5-tetrazolyl)-4-methyl-2-pyridinecarboxamide is thereby obtained.

M.p. 241.5°–242.5° C. (decomp.)

Sodium salt: M.p. 210°–215° C. (decomp.)

EXAMPLE 3

(1) 4 g of 6-styryl-2-pyridinecarboxylic acid are dissolved in 60 ml of thionyl chloride, and the solution is refluxed for 2 hours. After the reaction, the mixture is concentrated under reduced pressure to remove excess thionyl chloride. The residue is dissolved in 10 ml of dimethylformamide, and a solution of 1.78 g of 5-aminotetrazole and 9 g of triethylamine in 9 ml of dimethylformamide is added thereto under cooling. The mixture is stirred at 70° C. for 2 hours. After the reaction, the mixture is concentrated under reduced pressure to remove dimethylformamide. Water is added to the residue, and the aqueous mixture is adjusted to pH 2 with 10% hydrochloric acid. The crystalline precipitates are collected by filtration and then recrystallized from a mixture of dimethylformamide and ethanol. 3.0 g of N-(5-tetrazolyl)-6-styryl-2-pyridinecarboxamide are thereby obtained.

M.p. 261.5°–262° C. (decomp.)

Sodium salt: M.p. >300° C.

(2) A mixture of 2 g of N-(5-tetrazolyl)-6-styryl-2-pyridinecarboxamide, 30 ml of water, 15 ml of ethanol, 5 ml of an aqueous 10% sodium hydroxide solution and 0.18 g of 10% palladium-on-carbon is shaken at 40° C. for 2 hours and then at room temperature for 15 hours in hydrogen gas stream under atmospheric pressure. After the reaction, ethanol is added to the mixture to dissolve the precipitates therein. Insoluble materials are filtered off, and the filtrate is adjusted to pH 3 with 10% hydrochloric acid. The crystalline precipitates are collected by filtration, washed with water, dried and then recrystallized from a mixture of dimethylformamide and ethanol. 1.34 g of N-(5-tetrazolyl)-6-phenethyl-2-pyridinecarboxamide are thereby obtained.

M.p. 220°–221° C. (decomp.)

Sodium salt: M.p. 288°–289° C. (decomp.)

EXAMPLE 4

2.82 g of 5-methyl-2-pyridinecarboxylic acid, 20 ml of thionyl chloride and 2.3 g of 5-aminotetrazole are treated in the same manner as described in Example 1. The crude product thus obtained is recrystallized from dimethylformamide, whereby 1.5 g of N-(5-tetrazolyl)-5-methyl-2-pyridinecarboxamide are obtained.

M.p. 275°–277° C. (decomp.)

Sodium salt: M.p. >300° C.

EXAMPLE 5

2.3 g of 6-methyl-2-pyridinecarboxylic acid, 20 ml of thionyl chloride and 1.33 g of 5-aminotetrazole are treated in the same manner as described in Example 1. The crude product thus obtained is recrystallized from a mixture of dimethylformamide and ethanol, whereby 1.31 g of N-(5-tetrazolyl)-6-methyl-2-pyridinecarboxamide are obtained.

M.p. 248°–249° C. (decomp.)

Sodium salt: M.p. 295°–297° C. (decomp.)

EXAMPLE 6

1.9 g of 6-n-propyl-2-pyridinecarboxylic acid, 12 ml of thionyl chloride and 0.96 g of 5-aminotetrazole are treated in the same manner as described in Example 1. The crude product thus obtained is recrystallized from a mixture of dimethylformamide and water, whereby 0.26 g of N-(5-tetrazolyl)-6-n-propyl-2-pyridinecarboxamide is obtained.

M.p. 218°–220° C. (decomp.)

Sodium salt: M.p. 300°–303° C. (decomp.)

EXAMPLE 7

2.4 g of 6-n-butyl-2-pyridinecarboxylic acid, 15 ml of thionyl chloride and 0.97 g of 5-aminotetrazole are treated in the same manner as described in Example 1. The crude product thus obtained is recrystallized from a mixture of dimethylformamide and ethanol, whereby 0.97 g of N-(5-tetrazolyl)-6-n-butyl-2-pyridinecarboxamide is obtained.

M.p. 194°–197° C. (decomp.)

Sodium salt: M.p. 296°–297° C. (decomp.)

EXAMPLE 8

1.16 g of 4-chloro-2-pyridinecarboxylic acid, 25 ml of thionyl chloride and 0.82 g of 5-aminotetrazole are treated in the same manner as described in Example 1. The crude product thus obtained is recrystallized from a mixture of dimethylformamide and ethanol, whereby 1.0 g of N-(5-tetrazolyl)-4-chloro-2-pyridinecarboxamide is obtained.

M.p. 240°–250° C. (decomp.)

Sodium salt: The product begins to decompose at about 260° C.

EXAMPLE 9

0.53 g of 3-chloro-2-pyridinecarboxylic acid, 10 ml of thionyl chloride and 0.27 g of 5-aminotetrazole are treated in the same manner as described in Example 1. The crude product thus obtained is recrystallized from a mixture of dimethylformamide and ethanol, whereby 0.28 g of N-(5-tetrazolyl)-3-chloro-2-pyridinecarboxamide is obtained.

M.p. 252°–254° C. (decomp.)

Sodium salt: M.p. 210°–218° C. (decomp.) (The product begins to darken at about 70° C.).

EXAMPLE 10

0.46 g of 6-chloro-2-pyridinecarboxylic acid, 15 ml of thionyl chloride and 0.29 g of 5-aminotetrazole are treated in the same manner as described in Example 1. The crude product thus obtained is recrystallized from a mixture of dimethylformamide and water, whereby 0.17 g of N-(5-tetrazolyl)-6-chloro-2-pyridinecarboxamide is obtained.

M.p. 240°–247° C. (decomp.)

Sodium salt: M.p. >300° C.

EXAMPLE 11

1.45 g of 3-methoxy-2-pyridinecarboxylic acid, 30 ml of thionyl chloride and 0.95 g of 5-aminotetrazole are treated in the same manner as described in Example 1. The crude product thus obtained is recrystallized from a mixture of dimethylformamide and water, whereby 0.18 g of N-(5-tetrazolyl)-3-methoxy-2-pyridinecarboxamide is obtained.

M.p. 213.5°–215.5° C. (decomp.)

Sodium salt: M.p. 269°–271° C. (decomp.)

EXAMPLE 12

1.67 g of 4-methoxy-2-pyridinecarboxylic acid, 20 ml of thionyl chloride and 1.2 g of 5-aminotetrazole are treated in the same manner as described in Example 1. The crude product thus obtained is recrystallized from ethanol, whereby 0.28 g of N-(5-tetrazolyl)-4-methoxy-2-pyridinecarboxamide is obtained.

M.p. 235°–250° C. (decomp.)

Analysis calculated for $C_8H_8O_2N_6 \cdot \frac{1}{2}H_2O$: C, 41.92; H, 3.96; N, 36.67. Found: C, 42.30; H, 3.66; N, 37.96.

Sodium salt: M.p. 205°–235° C. (decomp.)

EXAMPLE 13

0.94 g of 6-n-butoxy-2-pyridinecarboxylic acid, 10 ml of thionyl chloride and 0.48 g of 5-aminotetrazole are treated in the same manner as described in Example 1. The crude product thus obtained is recrystallized from a mixture of dimethylformamide, water and ethanol, whereby 0.77 g of N-(5-tetrazolyl)-6-n-butoxy-2-pyridinecarboxamide is obtained.

M.p. 203°–204° C. (decomp.)

Sodium salt: M.p. 311°–312° C. (decomp.)

EXAMPLE 14

0.36 g of 5-methylthio-2-pyridinecarboxylic acid, 6 ml of thionyl chloride and 0.18 g of 5-aminotetrazole are treated in the same manner as described in Example 1. The crude product thus obtained is recrystallized from a mixture of dimethylformamide and ethanol, whereby 0.17 g of N-(5-tetrazolyl)-5-methylthio-2-pyridinecarboxamide is obtained.

M.p. 275°–276° C. (decomp.)

Sodium salt: M.p. 215°–218° C. (decomp.)

EXAMPLE 15

0.72 g of 5-nitro-2-pyridinecarboxylic acid, 13 ml of thionyl chloride and 0.37 g of 5-aminotetrazole are treated in the same manner as described in Example 1. The crude product thus obtained is recrystallized from a mixture of dimethylformamide, ethanol and water, whereby 0.51 g of N-(5-tetrazolyl)-5-nitro-2-pyridinecarboxamide is obtained.

M.p. 274°–275° C. (decomp.)

EXAMPLE 16

1.44 g of 4-nitro-6-methyl-2-pyridinecarboxylic acid, 27 ml of thionyl chloride and 0.79 g of 5-aminotetrazole are treated in the same manner as described in Example 1. The crude product thus obtained is washed with ethanol, whereby 0.79 g of N-(5-tetrazolyl)-4-nitro-6-methyl-2-pyridinecarboxamide is obtained.

M.p. >300° C.

Sodium salt: The product begins to decompose at about 200° C.

EXAMPLE 17

0.46 g of 4-ethyl-2-pyridinecarboxylic acid, 0.5 g of N,N'-carbonyldiimidazole and 0.28 g of 5-aminotetrazole are treated in the same manner as described in Example 2. The crude product thus obtained is recrystallized from a mixture of dimethylformamide and water, whereby 0.16 g of N-(5-tetrazolyl)-4-ethyl-2-pyridinecarboxamide is obtained.

M.p. 217°–218° C. (decomp.)

Sodium salt: The product begins to decompose at about 190° C.

EXAMPLE 18

0.42 g of 4-isopropyl-2-pyridinecarboxylic acid, 0.42 g of N,N'-carbonyldiimidazole and 0.24 g of 5-aminotetrazole are treated in the same manner as described in Example 2. The crude product thus obtained is recrystallized from a mixture of dimethylformamide and water, whereby 0.17 g of N-(5-tetrazolyl)-4-isopropyl-2-pyridinecarboxamide is obtained.

M.p. 198°–203° C. (decomp.)

Sodium salt: M.p. 205°–209° C. (decomp.)

EXAMPLE 19

0.52 g of 4-n-butyl-2-pyridinecarboxylic acid, 0.48 g of N,N'-carbonyldiimidazole and 0.27 g of 5-aminotetrazole are treated in the same manner as described in Example 2. The crude product thus obtained is recrystallized from a mixture of dimethylformamide, water and ethanol, whereby 0.45 g of N-(5-tetrazolyl)-4-n-butyl-2-pyridinecarboxamide is obtained.

M.p. 218°–219° C. (decomp.)

Sodium salt: M.p. 275°–278° C. (decomp.)

EXAMPLE 20

1.49 g of 3-methyl-2-pyridinecarboxylic acid, 1.8 g of N,N'-carbonyldiimidazole and 1.2 g of 5-aminotetrazole are treated in the same manner as described in Example 2. The crude product thus obtained is recrystallized from a mixture of dimethylformamide and ethanol, whereby 0.2 g of N-(5-tetrazolyl)-3-methyl-2-pyridinecarboxamide is obtained.

M.p. 227°–230° C. (decomp.)

Sodium salt: M.p. 285°–295° C. (decomp.)

EXAMPLE 21

0.81 g of 4.6-dimethyl-2-pyridinecarboxylic acid, 0.86 g of N,N'-carbonyldiimidazole and 0.54 g of 5-aminotetrazole are treated in the same manner as described in Example 2. The crude product thus obtained is recrystallized from a mixture of dimethylformamide and ethanol, whereby 0.47 g of N-(5-tetrazolyl)-4,6-dimethyl-2-pyridinecarboxamide is obtained.

M.p. 247°–248° C. (decomp.) (The product begins to become moistened at 230° C.).

Sodium salt: M.p. 241°–265° C. (decomp.) (The product begins to become moistened at 210° C.).

EXAMPLE 22

0.76 g of 3,6-dimethyl-2-pyridinecarboxylic acid, 0.82 g of N,N'-carbonyldiimidazole and 0.51 g of 5-aminotetrazole are treated in the same manner as described in Example 2. The crude product thus obtained is recrystallized from a mixture of dimethylformamide and ethanol, whereby 0.68 g of N-(5-tetrazolyl)-3,6-dimethyl-2-pyridinecarboxamide is obtained.

M.p. 269°–272° C. (decomp.)

Sodium salt: M.p. 295°–297° C. (decomp.) (The product begins to become moistened at 210° C.).

EXAMPLE 23

0.55 g of 5,6-dimethyl-2-pyridinecarboxylic acid, 0.77 g of N,N'-carbonyldiimidazole and 0.48 g of 5-aminotetrazole are treated in the same manner as described in Example 2. The crude product thus obtained is recrystallized from a mixture of dimethylformamide and ethanol, whereby 0.44 g of N-(5-tetrazolyl)-5,6-dimethyl-2-pyridinecarboxamide is obtained.

M.p. 240°–242° C. (decomp.)

Sodium salt: M.p. >300° C.

EXAMPLE 24

0.3 g of 4-bromo-2-pyridinecarboxylic acid, 0.25 g of N,N'-carbonyldiimidazole and 0.14 g of 5-aminotetrazole are treated in the same manner as described in Example 2. The crude product thus obtained is recrystallized from a mixture of dimethylformamide and ethanol, whereby 0.24 g of N-(5-tetrazolyl)-4-bromo-2-pyridinecarboxamide is obtained.

M.p. 250°–280° C. (decomp.) (The product begins to turn red at about 240° C.).

Sodium salt: M.p. 180°–220° C. (decomp.)

EXAMPLE 25

0.89 g of 6-bromo-2-pyridinecarboxylic acid, 0.71 g of N,N-carbonyldiimidazole and 0.41 g of 5-aminotetrazole are treated in the same manner as described in Example 2. The crude product thus obtained is recrystallized from a mixture of dimethylformamide and water, whereby 0.67 g of N-(5-tetrazolyl)-6-bromo-2-pyridinecarboxamide is obtained.

M.p. 230°–231.5° C. (decomp.)

Sodium salt: M.p. >300° C.

EXAMPLE 26

0.48 g of 6-methoxy-2-pyridinecarboxylic acid, 0.51 g of N,N'-carbonyldiimidazole and 0.29 g of 5-aminotetrazole are treated in the same manner as described in Example 2. The crude product thus obtained is recrystallized from a mixture of dimethylformamide, water and ethanol, whereby 0.32 g of N-(5-tetrazolyl)-6-methoxy-2-pyridinecarboxamide is obtained.

M.p. 252°–253° C. (decomp.)

Sodium salt: M.p. 288°–290° C. (decomp.)

EXAMPLE 27

0.25 g of 6-phenoxy-2-pyridinecarboxylic acid, 0.2 g of N,N'-carbonyldiimidazole and 0.11 g of 5-aminotetrazole are treated in the same manner as described in Example 2. The crude product thus obtained is recrystallized from ethanol, whereby 0.13 g of N-(5-tetrazolyl)-6-phenoxy-2-pyridinecarboxamide is obtained.

M.p. 212°–218° C. (decomp.) (The product begins to become moistened at 190° C.).

Sodium salt: M.p. 290°–296° C. (decomp.)

EXAMPLE 28

0.48 g of 4-nitro-2-pyridinecarboxylic acid, 0.48 g of N,N'-carbonyldiimidazole and 0.27 g of 5-aminotetrazole are treated in the same manner as described in Example 2. The crude product thus obtained is recrystallized from ethanol, whereby 0.38 g of N-(5-tetrazolyl)-4-nitro-2-pyridinecarboxamide is obtained.

M.p. 250°–270° C. (decomp.)

Sodium salt: M.p. 260°–280° C. (decomp.)

EXAMPLE 29

0.68 g of 4-chloro-6-methyl-2-pyridinecarboxylic acid, 0.67 g of N,N'-carbonyldiimidazole and 0.37 g of 5-aminotetrazole are treated in the same manner as described in Example 2. The crude product thus obtained is recrystallized from a mixture of dimethylformamide and ethanol, whereby 0.65 g of N-(5-tetrazolyl)-4-chloro-6-methyl-2-pyridinecarboxamide is obtained.

M.p. 240°–250° C. (decomp.) (The product begins to become moistened at about 150° C.).

Sodium salt: M.p. 305°–310° C. (decomp.)

EXAMPLE 30

0.8 g of 4-methoxy-6-methyl-2-pyridinecarboxylic acid, 0.82 g of N,N'-carbonyldiimidazole and 0.45 g of 5-aminotetrazole are treated in the same manner as described in Example 2. The crude product thus obtained is recrystallized from a mixture of dimethylformamide and ethanol, whereby 0.82 g of N-(5-tetrazolyl)-4-methoxy-6-methyl-2-pyridinecarboxamide is obtained.

M.p. 252°–258° C. (decomp.)

Sodium salt: M.p. 200°–210° C. (decomp.)

What we claim is:

1. A 2-pyridinecarboxamide derivative of the formula:

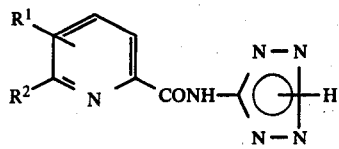

wherein $R^1$ is hydrogen, lower alkyl, lower alkoxy or halogen and is in the 3rd-, 4th- or 5th-position of the pyridyl group, and $R^2$ is hydrogen, lower alkyl, lower alkoxy, phenyl-lower alkyl, phenyl-lower alkenyl or halogen, or a pharmaceutically acceptable salt thereof.

2. The 2-pyridinecarboxamide derivative claimed in claim 1, in which $R^1$ is hydrogen, lower alkyl or halogen and is in the 3rd- or 4th-position of the pyridyl group, and $R^2$ is hydrogen, lower alkyl or phenyl-lower alkenyl.

3. The 2-pyridinecarboxamide derivative claimed in claim 2, in which $R^1$ is hydrogen, methyl, ethyl, chloro or bromo, and $R^2$ is hydrogen, methyl or styryl.

4. The 2-pyridinecarboxamide derivative claimed in claim 3, in which $R^1$ is methyl, ethyl, chloro or bromo, and $R^2$ is hydrogen.

5. The 2-pyridinecarboxamide derivative claimed in claim 3, in which $R^1$ is hydrogen, methyl or chloro, and $R^2$ is methyl or styryl.

6. The 2-pyridinecarboxamide derivative claimed in claim 5, in which $R^2$ is methyl.

7. The compound claimed in claim 4, which is N-(5-tetrazolyl)-4-chloro-2-pyridinecarboxamide or a pharmaceutically acceptable salt thereof.

8. The compound claimed in claim 5 which is N-(5-tetrazolyl)-6-styryl-2-pyridinecarboxamide or a pharmaceutically acceptable salt thereof.

9. The compound of claim 6 which is N-(5-tetrazolyl)-6-methyl-2-pyridinecarboxamide or a pharmaceutically acceptable salt thereof.

10. The compound claimed in claim 6 which is N-(5-tetrazolyl)-3,6-dimethyl-2-pyridinecarboxamide or pharmaceutically acceptable salt thereof.

11. The compound claimed in claim 6 which is N-(5-tetrazolyl)-4-chloro-6-methyl-2-pyridinecarboxamide or a pharmaceutically acceptable salt thereof.

12. An anti-allergic pharmaceutical composition which comprises a therapeutically effective amount of a derivative of claim 1 and a pharmaceutically acceptable carrier therefor.

13. A method of treatment of allergic symptoms in a warm-blooded animal which comprises administering thereto a therapeutically effective amount of a derivative of claim 1.

14. The method according to claim 13 wherein $R^1$ is hydrogen, lower alkyl, lower alkoxy or halogen and is in the 3rd-, 4th- or 5th-position of the pyridyl group, and $R^2$ is hydrogen, lower alkyl, lower alkoxy, phenyl-lower alkyl, phenyl-lower alkenyl or halogen.

15. The method according to claim 14, wherein $R^1$ is hydrogen, lower alkyl or halogen and is in the 3rd- or 4th- position of the pyridyl group, and $R^2$ is hydrogen, lower alkyl or phenyl-lower alkenyl.

16. The method according to claim 15 wherein $R^1$ is hydrogen, methyl, ethyl, chloro or bromo, and $R^2$ is hydrogen, methyl or styryl.

17. The method according to claim 16, wherein $R^1$ is methyl, ethyl, chloro or bromo, and $R^2$ is hydrogen.

18. The method according to claim 16, wherein $R^1$ is hydrogen, methyl or chloro, and $R^2$ is methyl or styryl.

19. The method according to claim 18, wherein $R^2$ is methyl.

20. The method according to claim 17, wherein N-(5-tetrazolyl)-4-chloro-2-pyridinecarboxamide or a pharmaceutically acceptable salt thereof is administered.

21. The method according to claim 18, wherein N-(5-tetrazolyl)-6-styryl-2-pyridinecarboxamide or a pharmaceutically acceptable salt thereof is administered.

22. The method according to claim 19, wherein N-(5-tetrazolyl)-6-methyl-2-pyridinecarboxamide or a pharmaceutically acceptable salt thereof is administered.

23. The method according to claim 19, wherein N-(5-tetrazolyl)-3,6-dimethyl-2-pyridinecarboxamide or a pharmaceutically acceptable salt thereof is administered.

24. The method according to claim 19, wherein N-(5-tetrazolyl)-4-chloro-6-methyl-2-pyridinecarboxamide or a pharmaceutically acceptable salt thereof is administered.

* * * * *